United States Patent [19]

Deeg et al.

[11] Patent Number: 4,503,144

[45] Date of Patent: Mar. 5, 1985

[54] METHOD AND COMPOSITION FOR THE DETERMINATION OF CHOLESTEROL

[75] Inventors: Rolf Deeg, Seeshaupt; Helmut Schlumberger, Polling; Joachim Ziegenhorn, Starnberg, all of Fed. Rep. of Germany

[73] Assignee: Boehringer Mannheim GmbH, Mannheim-Waldhof, Fed. Rep. of Germany

[21] Appl. No.: 328,350

[22] Filed: Dec. 7, 1981

[30] Foreign Application Priority Data

Dec. 8, 1980 [DE] Fed. Rep. of Germany ....... 3046241

[51] Int. Cl.³ .................. C12Q 1/60; C12Q 1/44; C12Q 1/26; C12Q 1/28; C12R 1/465
[52] U.S. Cl. .................................. 435/11; 435/19; 435/25; 435/28; 435/805; 435/810; 435/886
[58] Field of Search .................. 435/11, 19, 25, 27, 435/28, 805, 810, 886

[56] References Cited

U.S. PATENT DOCUMENTS

| | | | |
|---|---|---|---|
| 3,983,005 | 9/1976 | Goodhue et al. | 435/11 |
| 4,212,938 | 7/1980 | Gruber et al. | 435/11 |
| 4,226,713 | 10/1980 | Goldberg | 435/11 |
| 4,229,527 | 10/1980 | Ziegenhorn et al. | 435/11 |
| 4,350,762 | 9/1982 | DeLuca | 435/11 |

FOREIGN PATENT DOCUMENTS 4857 10/1979 European Pat. Off. .
16946 10/1980 European Pat. Off. .

OTHER PUBLICATIONS

Otani et al., *Chemical Abstracts*, 87: 80812a, 257, (1977).
Otani et al., Chem. Pharm. Bull., 25(6): 1452–1455, (1977).
Tomioka et al., J. Biochem., 79: 903–915, (1976).

*Primary Examiner*—Esther M. Kepplinger
*Attorney, Agent, or Firm*—Felfe & Lynch

[57] ABSTRACT

The present invention provides a process for the determination of cholesterol in free or bound form by means of cholesterol oxidase and optionally of cholesterol esterase by measurement of the oxygen consumption, of the hydrogen peroxide formed or of the cholestenone formed, wherein the determination is carried out kinetically with the use of a cholesterol oxidase which has been obtained from a micro-organism of the genus Streptomyces and with the addition of 3,4-dichlorophenol.

The present invention also provides a reagent for the kinetic determination of cholesterol, comprising cholesterol oxidase and a system for the determination of hydrogen peroxide or of cholestenone and optionally cholesterol esterase, wherein it additionally contains 3,4-dichlorophenol and the cholesterol oxidase used originates from a micro-organism of the genus Streptomyces.

18 Claims, No Drawings

METHOD AND COMPOSITION FOR THE DETERMINATION OF CHOLESTEROL

This invention relates to a method and a reagent for the determination of cholesterol, using cholesterol oxidase.

It is known to react cholesterol, possibly after previous liberation from its esters by chemical or enzymatic saponification, by means of cholesterol oxidase in the presence of molecular oxygen to give cholestenone and hydrogen peroxide and to utilise these quantitatively proceeding reactions for the determination of the cholesterol, either the cholestenone or hydrogen peroxide formed or the consumed oxygen thereby being measured. This enzymatic cholesterol determination process has admittedly brought a considerable advance due to its specificity in comparison with the previously used chemical methods of determination but hitherto the process has not been suitable for a rapid and practical kinetic carrying out. Because of the low $K_M$ value of cholesterol oxidase, which catalyses the most specific part of the reaction sequence, the reaction in the concentration range of up to 13 mMol/l., which is of interest for the determination of cholesterol, does not proceed according to the first or pseudo-first order. However, such a course of reaction is a prerequisite for a rapid and practical kinetic method of determination which does not require a sample blank value, which would make possible a substantial shortening of the time requirement per individual analysis in comparison with the previously necessary end point or kinetic methods. The time requirement for the previous photometric processes was from 10 to 6 minutes and, in the case of kinetic methods, analysis times of 1 to 3 minutes are desired. The most modern automatic analysers are intended for a high sample throughput and permit only short incubation times which could not be achieved with the previous processes used for the detection of cholesterol. Consequently, the automatic analysers with high analysis frequency which are today usual cannot be fully utilised.

Therefore, it is an object of the present invention to provide a kinetic process of determination for the cholesterol oxidase reaction in which this proceeds according to the pseudo-first order.

It is known that, in many cases, it is possible to achieve such a course of reaction at too low $K_M$ values of the enzymes involved by an artificial increase of the $K_M$ value. From the theory of Michaelis and Menton, it follows that enzyme-catalysed single substrate reactions then proceed over a wide concentration range according to the first order when the Michaelis constant of the enzyme is very much greater than the maximum substrate concentration. Since the previously known cholesterol oxidases from different microorganism genuses, such as Nocardia, Brevibacterium or Streptomycetes, have $K_M$ values of the order of $10^{-4}$ to $10^{-5}$ mol/l., only low cholesterol concentrations can here be measured. Attempts artificially to increase the $K_M$ value of the cholesterol oxidase in known manner by the addition of a competitive inhibitor proved to be unsuccessful.

Surprisingly, however, we have now found that it is possible, in the case of the selection of a cholesterol oxidase of particular origin and of a particular phenol derivative, to achieve a course of reaction according to the pseudo-first order.

Thus, according to the present invention, there is provided a process for the determination of cholesterol in free or bound form by means of cholesterol oxidase and optionally of cholesterol esterase by measurement of the oxygen consumption, of the hydrogen peroxide formed or of the cholestenone formed, wherein the determination is carried out kinetically with the use of a cholesterol oxidase which has been obtained from a micro-organism of the genus Streptomyces and with the addition of 3,4-dichlorophenol.

Neither with the cholesterol oxidases from Nocardia or Brevibacterium previously used for the determination of cholesterol nor with the steroids or bile acids similar to cholesterol, which are primarily considered as competitive inhibiting materials, could such a course of reaction be achieved which, for the first time, makes possible a kinetic determination. The other isomers of dichlorophenol also have no or only an insufficient influence on the course of the reaction. Therefore, it is assumed that a special exchange action occurs between the 3,4-dichlorophenol and the enzyme from the micro-organisms of the genus Streptomyces.

The obtaining of cholesterol oxidase from Streptomycetes is described in Federal Republic of Germany Patent Specification No. 2,924,875. Examples of suitable strains include *Streptomyces griseofuscus* DSM 40191, *Streptomyces hygroscopicus* DSM 40771 and *Streptomyces acidomyceticus* DSM 40798.

The aimed for course of reaction of the first order can be achieved with widely varying concentrations of 3,4-dichlorophenol and cholesterol oxidase. However, it is preferable to use 0.5 to 10 mmol/liter 3,4-dichlorophenol and 0.1 to $20 \times 10^3$ U/liter cholesterol oxidase from Streptomyces.

The process of the present invention is otherwise carried out in the usual manner for kinetic determinations. Preferably, at least two measurements are carried out in a previously determined time interval. The determination can be carried out in the whole pH value range in which the cholesterol oxidase from Streptomyces is active, with the proviso that any adjuvant enzymes possibly used are also active in this pH range. The determination is preferably carried out in a buffered solution at a pH value of from 6.5 to 8.

As already mentioned, in principle all known variants of the cholesterol determination with the use of cholesterol oxidase can be used in the scope of the present invention. Only the measurement of the cholestenone formation at 230 to 250 nm is less suitable in the case of comparatively high 3,4-dichlorophenol concentrations since 3,4-dichlorophenol then absorbs at the measurement wavelength of the cholestenone. Therefore, in the case of this embodiment of the process according to the present invention, a concentration of 1.5 mmol/liter of 3,4-dichlorophenol should not be exceeded.

One preferred embodiment of the process according to the present invention consists in the determination of the hydrogen peroxide formed by the addition of 4-aminoantipyrine, phenol, peroxidase and a buffer substance appropriate for this system, preferred buffers including phosphate buffer, hepes buffer (hepes: 4-(2-hydroxyethyl)-1-piperazinoethane-sulphonic acid) and tris buffer.

In the case of this embodiment of the present invention, the best results are obtained when, in addition, a non-ionic detergent and optionally also a detergent of the cholic acid group is added.

The present invention also provides a reagent for the kinetic determination of cholesterol, comprising cholesterol oxidase and a system for the determination of hydrogen peroxide or of cholestenone and optionally cholesterol esterase, wherein it additionally contains 3,4-dichlorophenol and the cholesterol oxidase originates from a micro-organism of the genus Streptomyces.

A preferred system for the determination of hydrogen peroxide is a combination of 4-aminoantipyrine or of a derivative thereof, phenol or a phenol derivative, buffer and detergent, this system frequently being referred to as the PAP system. Therefore, the PAP system and the modifications thereof are especially advantageous because the coloured material formed absorbs in ultra-violet light at wavelengths other than that of 3,4-dichlorophenol so that no impairment of the sensitivity can arise due to overlapping of the extinctions. The presence of a non-ionic detergent has proved to be especially appropriate, which may be used alone or optionally together with a detergent of the cholic acid group.

The reagent according to the present invention preferably contains a buffer substance; all buffers can be used which are able to buffer in the activity range of the participating enzymes and preferably in the pH range of from 6.5 to 8. Phosphate buffer, hepes buffer and tris buffer have proved to be especially useful.

A reagent according to the present invention which has proved to be especially preferred is one which, as the system for determining hydrogen peroxide, contains the PAP system and has the following quantitative composition:

0.1 to $10 \times 10^3$ U/l. cholesterol oxidase,
0.1 to $20 \times 10^3$ U/l. cholesterol esterase,
0.1 to $5 \times 10^3$ U/l. peroxidase,
1 to 10 mmol/l. 3,4-dichlorophenol, 0.5 to 10 mmol/l. 4-aminoantipyrine,
5 to 20 mmol/l. phenol or phenol derivative,
1 to 10 g./l. non-ionic detergent,
0 to 15 mmol/l. detergent of the cholic acid group and
50 to 200 mmol/l. buffer, pH 6.5 to 8.

In addition, the reagent according to the present invention can also contain additional materials usual for enzymatic reagents, such as stabilising agents, for example mannitol, bactericides, such as azides, and inorganic salts.

In the above-mentioned PAP system according to Trinder, instead of phenol, there can be used phenol derivatives, aniline derivatives, naphthol, naphthol derivatives, naphthylamine, naphthylamine derivatives, aminoquinolines, hydroxyquinolines, dihydroxyphenylacetic acid and similarly reacting substances. The 4-aminoantipyrine can be replaced, for example, by phenylenediamine-sulphonic acid, methylbenzothiazolone-hydrazone, sulphonated methylbenzothiazolone-hydrazone derivatives and similarly constituted compounds.

However, instead of the PAP system, according to the present invention other known hydrogen peroxide determination systems can also be employed. These include the luminescent methods in which the fluorescence or chemi-luminescence is measured, preferably, for example, the peroxidase/luminol system. Other appropriate systems comprise catalase, a $\beta$-diketone, for example acetylacetone, and an alcohol, for example methanol, ethanol or methylene glycol. Another appropriate system comprises peroxidase and a chromophore, such as 2,3'-aminobenzthiazoline-sulphonic acid.

When the reagent according to the present invention contains a system for the determination of cholestenone, then the known detection systems for this purpose can be used. If desired, as already mentioned above, the cholestenone formation can also be measured directly at 240 nm if a certain loss of sensitivity is not important since, at this wavelength, the 3,4-dichlorophenol also absorbs.

The reagent according to the present invention can also be present impregnated on to a solid carrier. In this case, the determination can be carried out either (a) by dipping the carrier impregnated with the reagent into the sample, or
(b) by dropping a definite amount of sample on to the reagent carrier, or
(c) by eluting the reagent from the carrier with a definite volume of sample.

If the rate of reaction is measured directly on the carrier, then this is possible, for example, reflectometrically or by the measurement of the luminescence. If the determination takes place after elution of the reagent, then the measurement can be carried out as in the case of the use of a carrier-free reagent.

The carrier materials for the analytical detection reagents are the conventional carriers, such as paper, cellulose, fibre fleece, porous synthetic resin membranes and the like. They can be produced by immersion into or spraying with the reagent according to the present invention.

The process according to the present invention permits a substantially quicker ascertainment of the amount of cholesterol in a sample and leads to a great saving of time, in comparison with conventional analysis processes. For automated analysis systems, in many cases the enzymatic determination of cholesterol hereby becomes a practicable possibility for the first time.

The following Examples are given for the purpose of illustrating the present invention:

EXAMPLE 1

The following reagent was employed:
500 U/l. cholesterol oxidase from Streptomyces,
1500 U/l. peroxidase,
800 U/l. cholesterol esterase,
5 mmol/l. 3,4-dichlorophenol,
5 mmol/l. phenol,
1 mmol/l. 4-aminophenazone,
4.8 g./l. non-ionic detergent (Genapol OX 100),
9.4 mmol/l. sodium desoxycholate,
200 mmol/l. phosphate buffer, pH 7.8.

On a commercially available automatic analyser (commercially available under the designation Centrifi-Chem 400), in the case of the following adjustment, the cholesterol determination in serum is carried out: temperature: 25° C.; filter: 500 nm; $t_0$-time delay: 60 seconds; $\Delta_t$-interval: 1 minute; blank, auto; test mode: term; print out: conc.; standard value: rated value Precilip; test code: oo reagent volume: 350 µl.; sample: 5 µl.; sample and water: 30 µl.

The determination gave a linear course of the curve up to at least 13 mmol/l.

The cholesterol oxidase used was obtained from *Streptomyces griseofuscus* DSM 40191.

EXAMPLE 2

The following reagent was used:

500 U/l. cholesterol oxidase from Streptomyces,
1500 U/l. cholesterol esterase,
1500 U/l. peroxidase,
5 mmol/l. 3,4-dichlorophenol,
5 mmol/l. phenol,
1 mmol/l. 4-aminophenazone,
4 g./l. isotridecyl ether,
100 mmol/l. tris buffer, pH 7.7.

The reagent was used as described in Example 1 on a commercially available automatic analyser (Centrifi-Chem 400) for the determination of cholesterol in serum. Here, too, a linear course was ascertained at least up to 13 mmol/l.

Analogous results were achieved on another automatic analyser (Eppendorff ACP 5040). In this case, a start reagent with 5 U/ml. cholesterol oxidase was used.

EXAMPLE 3

The following reagent was used:
500 U/l. cholesterol oxidase from Streptomyces,
1500 U/l. cholesterol esterase,
1500 U/l. peroxidase,
5 mmol/l. 3,4-dichlorphenol,
14 mmol/l. salicyl alcohol,
0.5 mmol/l. 4-aminophenazone,
4 g./l. isotridecyl ether,
10 mmol/l. sodium cholate,
50 mmol/l. hepes buffer, pH 6.9.

With this reagent, results were obtained analogous to those in Examples 1 and 2. The precision in the series which was achieved on both of the above-mentioned automatic analysers is shown by the following Table.

TABLE

| CentrifiChem 400 | ACP 5040 |
| --- | --- |
| n = 8 | n = 8 |
| x̄ = 311.3 | x̄ = 285.6 |
| S = 6.84 | S = 2.13 |
| CV = 2.20% | CV = 0.8% |

EXAMPLE 4

Kinetic determination with measurement of the cholestenone at 240 nm

| Reagent: | tris buffer | 0.1 mol/l., pH 7.6 |
| --- | --- | --- |
| | isotridecyl ether | 3 g./l. |
| | 3,4-dichlorophenol | 1.0 mmol/l. |
| | sodium cholate | 10.0 mmol/l. |
| | cholesterol oxidase | 0.2 U/ml. |

Batch: 2 ml. reagent, 10 μl. sample (cholesterol standard)
Test conditions:
T 25°
$E_1$ 1 min. after start of the reaction
$E_2$ 2 min. after start of the reaction
Result: cholesterol concentration/extinction change

| 2.59 mmol/l. | 30 mE |
| --- | --- |
| 5.17 mmol/l. | 60 mE |
| 10.34 mmol/l. | 120 mE |

EXAMPLE 5

Measurement of the oxygen consumption

| Reagent: | tris buffer | 0.1 mol/l., pH 7.6 |
| --- | --- | --- |
| | isotridecyl ether | 3 g./l. |
| | 3,4-dichlorophenol | 3 mmol/l. |
| | sodium cholate | 10 mmol/l. |
| | cholesterol oxidase | 2 U/ml. |

Batch: 1.5 ml. reagent, 10 μl. sample
Test conditions: T: 25° C.

The rate of the oxygen consumption is measured between the 2nd and 3rd minute. Result: cholesterol concentration/relative reaction rate

| 2.59 mmol/l. | 25 |
| --- | --- |
| 5.17 mmol/l. | 50 |
| 10.34 mmol/l. | 100 |

It will be understood that the specification and examples are illustrative but not limitative of the present invention and that other embodiments within the spirit and scope of the invention will suggest themselves to those skilled in the art.

What is claimed is:

1. Method for the determination of cholesterol in free or bound form by utilizing cholesterol oxidase, which method comprises contacting a sample with cholesterol oxidase, determining cholesterol contained in the sample kinetically with the use of a cholesterol oxidase which has been obtained from a microorganism of the genus Streptomyces and with the addition of 3,4-dichlorophenol, and measuring the oxygen consumption, the hydrogen peroxide formed, or the cholestenone formed, as a measure of the cholesterol content of the sample said cholesterol oxidase and said 3,4-dichlorophenol being present in amounts sufficient to achieve a pseudo-first order reaction.

2. Method as claimed in claim 1, wherein cholesterol oxidase is used in conjunction with cholesterol esterase.

3. Method as claimed in claim 1, wherein 0.5–50 mmol/l. 3,4-dichlorophenol and $0.1-50 \times 10^3$ U/l. cholesterol oxidase are used.

4. Method as claimed in claim 1, wherein at least two measurements are carried out at a predetermined time interval.

5. Method as claimed in claim 1, wherein the reaction is carried out in a buffered solution at a pH value of 6.5 to 8.

6. Method as claimed in claim 1, wherein hydrogen peroxide is determined.

7. Method as claimed in claim 6, wherein the hydrogen peroxide is determined by use of 4-aminoantipyrine phenol, peroxidase and phosphate buffer, hepes buffer or tris buffer.

8. Method as claimed in claim 1, wherein a non-ionic detergent is also added.

9. Method as claimed in claim 8, wherein an additional detergent of the cholic acid group is added.

10. Method as claimed in claim 1, wherein the oxygen consumption is measured.

11. Method as claimed in claim 1, wherein the cholestenone formed is measured.

12. Reagent for the kinetic determination of cholesterol, comprising cholesterol oxidase, a system for the determination of hydrogen peroxide or of cholestenone, and 3,4-dichlorophenol, and wherein the cholesterol oxidase used is from a microorganism of the genus Streptomyces said cholesterol oxidase and said 3,4- dichlorophenol being present in sufficient concentrations to achieve a pseudo-first order reaction in a cholesterol determination.

13. Reagent as claimed in claim 12 also containing cholesterol esterase.

14. Reagent as claimed in claim 12, wherein the system for the determination of hydrogen peroxide comprises 4-aminoantipyrine, phenol or a derivative thereof, buffer and detergent.

15. Reagent as claimed in claim 12, additionally containing a non-ionic detergent alone or together with a detergent of the cholic acid group.

16. Reagent as claimed in claim 12 also containing phosphate buffer, hepes buffer or tris buffer.

17. Reagent as claimed in claim 14, comprising
0.1 to $10 \times 10^3$ U/l. cholesterol oxidase,
0.1 to $20 \times 10^3$ U/l. cholesterol esterase,
0.1 to $5 \times 10^3$ U/l. peroxidase,
1 to 10 mmol/l. 3,4-dichlorophenol,
0.5 to 10 mmol/l. 4-aminoantipyrine,
5 to 20 mmol/l. phenol or phenol derivative,
1 to 10 g./l. non-ionic detergent,
0 to 15 mmol/l. detergent of the cholic acid group,
50 to 200 mmol/l. buffer—pH 6.5–8.

18. Reagent as claimed in claim 12, impregnated onto a solid carrier.

* * * * *